(12) United States Patent
Bar-Cohen et al.

(10) Patent No.: US 9,418,647 B2
(45) Date of Patent: Aug. 16, 2016

(54) COMMUNICATION IN PIPES USING ACOUSTIC MODEMS THAT PROVIDE MINIMAL OBSTRUCTION TO FLUID FLOW

(71) Applicant: CALIFORNIA INSTITUTE OF TECHNOLOGY, Pasadena, CA (US)

(72) Inventors: Yoseph Bar-Cohen, Seal Beach, CA (US); Eric D. Archer, Pasadena, CA (US); Xiaoqi Bao, San Gabriel, CA (US); Stewart Sherrit, La Crescenta, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 241 days.

(21) Appl. No.: 13/913,044

(22) Filed: Jun. 7, 2013

(65) Prior Publication Data
US 2014/0153368 A1 Jun. 5, 2014

Related U.S. Application Data

(60) Provisional application No. 61/656,940, filed on Jun. 7, 2012.

(51) Int. Cl.
*G10K 11/18* (2006.01)
*E21B 47/14* (2006.01)
*G10K 11/34* (2006.01)
*A61B 8/00* (2006.01)
*E21B 47/18* (2012.01)

(52) U.S. Cl.
CPC .............. *G10K 11/18* (2013.01); *A61B 8/4483* (2013.01); *E21B 47/14* (2013.01); *E21B 47/18* (2013.01); *G10K 11/34* (2013.01); *A61B 8/4488* (2013.01)

(58) Field of Classification Search
CPC .................. E21B 47/16–47/18; E21B 21/101; E21B 21/182; G01V 11/002; A61B 8/4483–8/4488
See application file for complete search history.

(56) References Cited

U.S. PATENT DOCUMENTS

| 2,280,226 A | 4/1942 | Firestone |
| 2,483,821 A | 10/1949 | Firestone |
| 2,625,035 A | 1/1953 | Firestone |
| 3,004,425 A | 10/1961 | Henry |
| 3,936,791 A | 2/1976 | Kossoff |
| 4,215,426 A * | 7/1980 | Klatt ............................... 367/83 |

(Continued)

FOREIGN PATENT DOCUMENTS

RU 2312334 C2 12/2007

OTHER PUBLICATIONS

Sherrit, S. et al. "Solid Microhorn Arrays for Acoustic Impedance Matching" Proceedings of the SPIE 15th International Symposium on Smart Structures and Materials; Mar. 9-13, 2008; San Diego, CA. 10 pages.

(Continued)

*Primary Examiner* — Hai Phan
*Assistant Examiner* — Orlando Bousono
(74) *Attorney, Agent, or Firm* — Steinfl & Bruno LLP

(57) ABSTRACT

A plurality of phased array acoustic communication devices are used to communicate data along a tubulation, such as a well. The phased array acoustic communication devices employ phased arrays of acoustic transducers, such as piezoelectric transducers, to direct acoustic energy in desired directions along the tubulation. The system is controlled by a computer-based controller. Information, including data and commands, is communicated using digital signaling.

22 Claims, 10 Drawing Sheets

(56) References Cited

U.S. PATENT DOCUMENTS

| | | | |
|---|---|---|---|
| 4,307,613 A | 12/1981 | Fox | |
| 4,546,459 A * | 10/1985 | Congdon | 367/155 |
| 4,744,416 A * | 5/1988 | Bower | 166/253.1 |
| 4,890,268 A | 12/1989 | Smith et al. | |
| 5,056,067 A * | 10/1991 | Drumheller | 367/82 |
| 5,099,459 A * | 3/1992 | Smith | 367/153 |
| 5,289,433 A * | 2/1994 | Cowles et al. | 367/34 |
| 5,485,843 A * | 1/1996 | Greenstein et al. | 600/455 |
| 5,552,004 A * | 9/1996 | Lorraine et al. | 156/154 |
| 5,592,438 A * | 1/1997 | Rorden et al. | 367/83 |
| 5,850,369 A * | 12/1998 | Rorden et al. | 367/83 |
| 5,995,449 A * | 11/1999 | Green et al. | 367/83 |
| 6,178,827 B1 * | 1/2001 | Feller | 73/861.27 |
| 6,208,586 B1 * | 3/2001 | Rorden et al. | 367/35 |
| 6,554,826 B1 * | 4/2003 | Deardorff | 606/27 |
| 6,672,163 B2 | 1/2004 | Han et al. | |
| 7,950,451 B2 | 5/2011 | Alberty | |
| 9,080,438 B1 * | 7/2015 | McCoy | E21B 47/18 |
| 2002/0101373 A1 * | 8/2002 | Arndt et al. | 342/124 |
| 2004/0003658 A1 * | 1/2004 | Han et al. | 73/152.47 |
| 2005/0022987 A1 * | 2/2005 | Green et al. | 166/250.17 |
| 2005/0034530 A1 * | 2/2005 | Han et al. | 73/784 |
| 2005/0050956 A1 * | 3/2005 | Gysling et al. | 73/753 |
| 2005/0120799 A1 * | 6/2005 | Gysling et al. | 73/753 |
| 2005/0207279 A1 * | 9/2005 | Chemali et al. | 367/83 |
| 2005/0259512 A1 * | 11/2005 | Mandal | 367/10 |
| 2007/0001028 A1 * | 1/2007 | Gysling | 239/318 |
| 2007/0019506 A1 * | 1/2007 | Mandal et al. | 367/117 |
| 2007/0227727 A1 * | 10/2007 | Patel et al. | 166/250.01 |
| 2007/0227776 A1 * | 10/2007 | Huang et al. | 175/42 |
| 2008/0247273 A1 * | 10/2008 | Chemali et al. | 367/82 |
| 2009/0000859 A1 | 1/2009 | Wang et al. | |
| 2009/0073809 A1 | 3/2009 | Fink et al. | |
| 2010/0165788 A1 * | 7/2010 | Rayssiguier et al. | 367/25 |
| 2010/0198736 A1 * | 8/2010 | Marino | G01N 21/3504 705/308 |
| 2010/0257926 A1 * | 10/2010 | Yamate et al. | 73/152.23 |
| 2010/0309019 A1 * | 12/2010 | Shah et al. | 340/855.7 |
| 2011/0018735 A1 * | 1/2011 | Garcia-Osuna et al. | 340/854.4 |
| 2011/0080806 A1 * | 4/2011 | Normann | 367/35 |
| 2011/0149687 A1 * | 6/2011 | Rayssiguier et al. | 367/82 |
| 2011/0168446 A1 * | 7/2011 | Lemenager et al. | 175/50 |
| 2011/0176387 A1 * | 7/2011 | Froelich | 367/82 |
| 2012/0033528 A1 * | 2/2012 | Zhao et al. | 367/28 |
| 2012/0120767 A1 | 5/2012 | Vu et al. | |
| 2013/0272098 A1 * | 10/2013 | Cahalan et al. | 367/134 |

OTHER PUBLICATIONS

Sherrit, S. et al. "Micro-Horn Arrays for Ultrasonic Impedance Matching" NASA Tech Briefs; Sep. 2009; vol. 33; No. 9; pp. 19-20.

* cited by examiner

COMMUNICATION IN PIPES USING ACOUSTIC MODEMS THAT PROVIDE MINIMAL OBSTRUCTION TO FLUID FLOW

CROSS-REFERENCE TO RELATED APPLICATIONS

This application claims priority to and the benefit of U.S. provisional patent application Ser. No. 61/656,940 filed Jun. 7, 2012, which application is incorporated herein by reference in its entirety.

STATEMENT REGARDING FEDERALLY FUNDED RESEARCH OR DEVELOPMENT

The invention described herein was made in the performance of work under a NASA contract, and is subject to the provisions of Public Law 96-517 (35 USC 202) in which the Contractor has elected to retain title.

THE NAMES OF THE PARTIES TO A JOINT RESEARCH AGREEMENT

This invention resulted from work under a joint research agreement between NASA Jet Propulsion Laboratory and Chevron U.S.A. Inc. pursuant to 42 U.S.C. 2473(c)(5) and (6), section 203(c) of the National Aeronautics and Space Act of 1958, as amended.

INCORPORATION-BY-REFERENCE OF MATERIAL SUBMITTED ON A COMPACT DISC

NOT APPLICABLE.

FIELD OF THE INVENTION

The invention relates to communication apparatus and methods in general and particularly to acoustical communication apparatus and methods.

BACKGROUND OF THE INVENTION

The oil industry seeks to communicate data, information and command signals along their drill holes over great distances. Enabling such communication is a great challenge due to the narrow cross-section of their pipes and the need to avoid blocking the flow of oil and other fluids that flow along the pipes. Generally, for underwater applications acoustic modems are used in worldwide subsea applications and they transmit data wirelessly through the water. However, such modems use acoustic transmitters and receivers that communicate in unobstructed water paths and they are not applicable to oil pipes having narrow passages and complex geometry. The limitation of conventional transducers that are used by existing acoustic modems results from their directivity that is not designed for travel in such constrained environments as an oil filled pipeline. Therefore, interferences, reflections and mode conversions take place that make the signal analysis of the communication algorithms an enormously complex task.

In conventional drilling practice, it is useful to obtain data from sensors that can be located at the advancing drill bit, or that can be located at positions in the well bore. Some of the kinds of apparatus and the data that are of interest include accelerometers and magnetometers to measure the inclination and azimuth of the wellbore as the well is being drilled so that the well can reach an intended location, information about the condition and operation of the drill bit, geological and chemical information about the formations and their compositions as the well passes through them, such as density, porosity, electrical resistivity data, magnetic resonance data, temperature and pressure data, gamma ray data, and the like.

In conventional drilling practice, the data can be communicated from the measurement device to a data collection an operation control station at the top of the well, or in some instances, to a similar station that is remote from the well itself. The communication methods that are conventionally used include mud pulse telemetry, electromagnetic telemetry and wired drill pipe systems.

In mud pulse telemetry, a valve is used to control the rate of flow of drilling mud, which can cause a change in pressure if the valve is activated over a short time interval. The pulses can be used to send data as digital pulsed signals, typically at data rates of tens of Hertz or lower. In addition, because the mud is also used as a drilling fluid, starting and stopping the flow of mud can disrupt the drilling action of the drill.

In electromagnetic telemetry, an electrical connection is made to the drill pipe itself, and the sensor or data generator is separated from the drill pipe by insulation. A second electrical contact is placed in the ground near the well. The two contacts form the two electrodes of a dipole antenna. The voltage difference between the two contacts represents a signal is the received signal that can be analyzed. This system can provide data rates of about 10 bits per second that are carried on very low frequency waves in the range of units to tens of Hertz. Electromagnetic telemetry has a limited depth capability, typically a few thousand feet.

In wired systems, an electrical connection such as a coax cable is provided to carry signals. While such systems can provide extremely high data rates, maintaining electrical connectivity can be an issue. One such system, called the IntelliSery wired pipe network by National Oilwell Varco of 7909 Parkwood Circle Dr., Houston, Tex. 77036, is reported to provide data rates upwards of 1 megabit per second, using induction coils to connect successive drill pipe sections.

It is known in the prior art to use ultrasonic phased arrays for medical imaging and for industrial non-destructive testing (NDT). Medical sonograms are commonly made with specialized multi-element transducers (phased arrays) and their accompanying hardware and software, and provide detailed cross-sectional pictures of internal organs. Phased array systems are also used in industrial settings to provide visualization in common ultrasonic tests that include weld inspection, bond testing, thickness profiling, and in-service crack detection.

Phased array probes typically consist of a transducer assembly with from 16 to as many as 256 small individual elements that can each be pulsed separately. These may be arranged in a strip (linear array), a ring (annular array), a circular matrix (circular array), or a more complex shape. As is the case with conventional transducers, phased array probes may be designed for direct contact use, as part of an angle beam assembly with a wedge, or for immersion use with sound coupling through a water path. Transducer frequencies are most commonly in the range from 2 MHz to 10 MHz. A phased array system will also include a sophisticated computer-based instrument that is capable of driving the multi-element probe, receiving and digitizing the returning echoes, and plotting that echo information in various standard formats. Unlike conventional flaw detectors, phased array systems can sweep a sound beam through a range of refracted angles or along a linear path, or dynamically focus at a number of different depths, thus increasing both flexibility and capability in inspection setups. Ultrasonic non-destructive test apparatus, components, software and control circuitry are available from a number of manufacturers, including Olympus Corporation, GE Measurement and Control, National Instruments, Sonatest, Inc., Marietta Nondestructive Testing Inc., X-R-I Testing Division of X-Ray Industries, and others.

Mulhauser, in 1931, obtained a German patent for using ultrasonic waves, using two transducers to detect flaws in solids.

Also known in the prior art is Firestone, U.S. Pat. No. 2,280,226, issued Apr. 21, 1942, which is said to disclose a device for detecting the presence of inhomogeneities of density or elasticity in materials.

Also known in the prior art is Firestone, U.S. Pat. No. 2,483,821, issued Oct. 4, 1949, which is said to disclose the inspection of materials by supersonic waves.

Also known in the prior art is Firestone, U.S. Pat. No. 2,625,035, issued Jan. 13, 1953, which is said to disclose electromechanical transducers. and particularly to a piezoelectric crystal apparatus for sending and receiving supersonic wave trains.

Also known in the prior art is Henry, U.S. Pat. No. 3,004,425, issued Oct. 17, 1961, which is said to disclose piezoelectric transducers, such as natural quartz, and particularly when utilized with instruments, such as the Ultrasonic Reflectoscope, which employ the pulse echo technique of ultrasonic materials inspection.

Also known in the prior art is Kossoff, U.S. Pat. No. 3,936,791, issued Feb. 3, 1976, which is said to disclose apparatus for ultrasonic examination of objects, particularly in medical diagnostic examination, comprised of a phased array transducer capable of focusing the beam of ultrasonic pulses in the longitudinal plane of the transducer, and focusing means to focus the dimensions of the beam normal to the longitudinal plane.

Also known in the prior art is Fox, U.S. Pat. No. 4,307,613, issued Dec. 29, 1981, which is said to disclose an array of transducer segments is arranged in columns, each of which has a multiplicity of segments. The segments are wired to permit excitation by one or the other of two opposite phases of high-frequency signal, and groups of segments can be excited with the same phase to approximate the shape of an annular-ring phase-reversal zone plate. By changing the groupings of the elements that are similarly excited, the position of the focal region produced by the zone plate is translated in lateral position. A ferrite-core transformer is conveniently employed for both phase splitting and addition of the echo signals received by the device.

Also known in the prior art is Smith et al., U.S. Pat. No. 4,890,268, issued Dec. 26, 1989, which is said to disclose a two-dimensional ultrasonic phase array is a rectilinear approximation to a circular aperture and is formed by a plurality of transducers, arranged substantially symmetrical about both a first (X) axis and a second (Y) axis and in a plurality of subarrays, each extended in a first direction (i.e. parallel to the scan axis X) for the length of a plurality of transducers determined for that subarray, but having a width of a single transducer extending in a second, orthogonal (the out-of-scan-plane, or Y) direction to facilitate dynamic focussing and/or dynamic apodization. Each subarray transducer is formed of a plurality of sheets (part of a 2-2 ceramic composite) all electrically connected in parallel by a transducer electrode applied to juxtaposed first ends of all the sheets in each transducer, while a common electrode connects the remaining ends of all sheets in each single X-coordinate line of the array.

Also known in the prior art is Han et al., U.S. Pat. No. 6,672,163, issued Jan. 6, 2004, which is said to disclose a method and apparatus for in-situ characterization of downhole fluids in a wellbore using ultrasonic acoustic signals. Measurements of the speed of sound, attenuation of the signal, and acoustic back-scattering are used to provide qualitative and quantitative data as to the composition, nature of solid particulates, compressibility, bubble point, and the oil/water ratio of the fluid. The tool generally comprises three sets of acoustic transducers mounted perpendicular to the direction of the flow. These transducers are capable of operating at different frequencies so that the spectrum of the acoustic signal can be optimized. The apparatus is capable of operating downhole to provide real time information as to conditions in the well.

Also known in the prior art is Alberty, U.S. Pat. No. 7,950,451, issued May 31, 2011, which is said to disclose methods and apparatus that combine a measurement of the physical velocity of material within the annulus of a well between the drill pipe and the wall of the well with a measurement of the area of the flow as determined from a measurement of distance between the drill pipe and the wall of the hole to determine the actual material volumetric flow rate. Changes in volumetric flow rate at one or more points along the well can be used to determine the occurrence and location of well dysfunctions. This knowledge can then be used to make decisions about treating well dysfunctions which will lead to more efficient use of drilling rig time.

There is a need for improved systems and methods for communication along bore holes.

SUMMARY OF THE INVENTION

According to one aspect, the invention features an acoustic communication system for use in a tubulation. The system comprises a tubulation having a first end and at least a second end; a plurality of phased array acoustic communication devices, each of the plurality of phased array acoustic communication devices configured to send acoustic signals and to receive acoustic signals, a first one of the plurality of phased array acoustic communication devices situated proximate to the first end of the tubulation and having at least one input port for communication with a controller and having at least one output port for communication with the controller, and a second of the plurality of phased array acoustic communication devices situated at a distance from the first one of the plurality of phased array acoustic communication devices, the second of the plurality of phased array acoustic communication devices configured to communicate with and to receive instructions by way of the first the plurality of phased array acoustic communication devices; and a controller configured to activate the one of the plurality of phased array acoustic communication devices by way of the input port, configured to receive a signal from the one of the plurality of phased array acoustic communication devices by way of the output port input terminal and configured to provide at a controller output port an electrical signal representative of an acoustic signal received by the one of the plurality of phased array acoustic communication devices.

In one embodiment, the tubulation is a bore of a well.

In yet a further embodiment, the transducer system does not occlude or obstruct the bore of the well.

In another embodiment, wherein each of the plurality of phased array acoustic communication devices has a unique identifier used in communication between phased array acoustic communication devices.

In yet another embodiment, each of the plurality of phased array acoustic communication devices operates at an acoustic frequency different from the acoustic frequency of operation of all others of the plurality of phased array acoustic communication devices.

In still another embodiment, the well is an oil well.

In a further embodiment, the well is a gas well.

In an additional embodiment, the controller comprises a general purpose programmable computer and a set of instructions recorded in a non-transitory manner on a machine-readable medium.

In one more embodiment, the set of instructions when operating on the general purpose programmable computer activates the one of the plurality of phased array acoustic communication devices by way of the input port.

In still a further embodiment, the set of instructions when operating on the general purpose programmable computer controls the reception of a signal from the one of the plurality of phased array acoustic communication devices by way of the output port input terminal.

In one embodiment, the set of instructions when operating on the general purpose programmable computer controls the provision at a controller output port of an electrical signal representative of an acoustic signal received by the one of plurality of phased array acoustic communication devices.

In still another embodiment, the system further comprises a display.

In a further embodiment, the set of instructions when operating on the general purpose programmable computer controls the operation of the display.

In yet a further embodiment, the set of instructions when operating on the general purpose programmable computer controls the information that will be presented to a user.

In an additional embodiment, the system further comprises an input device operable by a user.

In one more embodiment, the set of instructions when operating on the general purpose programmable computer controls the receipt of input from a user.

In another embodiment, at least one of the plurality of phased array acoustic communication devices is in tubular form.

In still another embodiment, at least one of the plurality of phased array acoustic communication devices has an internal opening of at least the same cross section as the tubulation.

In yet a further embodiment, at least one of the plurality of phased array acoustic communication devices is in communication with a sensor.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

An acoustic modem that uses a plurality of separate phased-array transceivers (transmitters and receivers) is disclosed allowing the communication of high frequency acoustic waves sideways to the transducer along a fluid filled pipe. The disclosed acoustic transducer allows one to direct waves between the transmitter and the receiver with minimal interference introduced by the presence of the piping walls. In another embodiment, a system and method for directly sending communication signals up and down a bore hole is disclosed that uses angled piezoelectric ring transducers.

An acoustic phased array transducer is disclosed that improves communication along fluid filled pipes. The transducers are configured to transmit at a shallow angle to the surface with a narrow beam that can be directed so as to minimize interferences with the pipe geometry along the path to the receiver part of the modem.

We describe systems and methods of communication that are needed to transmit data from sensors, as well as control actuators in the completion zone of a well.

Transducers

Figure 1:
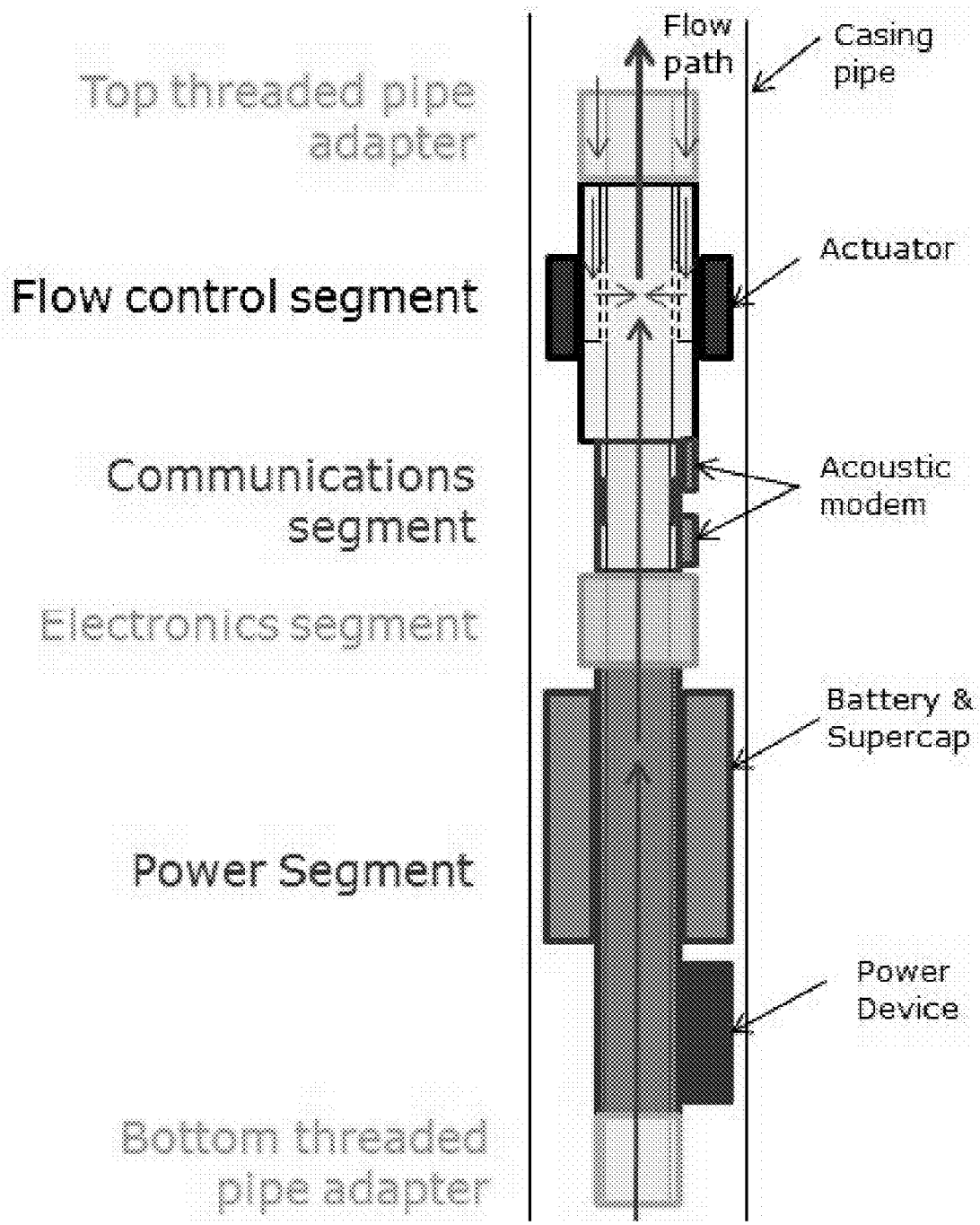
FIG. 1 is a schematic view of a pipe section of the system.

A general schematic view of a pipe section of the system is shown in FIG. 1.

In a working well or pipe, the fluid that is present can include crude oil, water, silt and chemicals. According to one embodiment, phased array transducers are used to generate waves and to transmit them parallel to the main direction of the pipe, so as to transmit acoustic waves along the flowing fluid. The phased array transducer allows one to design the system to operate at an appropriate frequency that is determined by cutoff frequency due to attenuation and the required baud rate. In practice, the higher the frequency the higher the baud rate and the higher the attenuation.

A volume expanding bidirectional acoustic projector can produce up- and down-hole ultrasonic/sonic communication signals. Since the liquid filled pipe forms a waveguide, different mode of waves may propagate in the liquid core with different phase and group velocities. In order to receive clear, less distorted signals, it is better to operate at the fundamental modes that can propagate through the fluid. For an ideal hard wall liquid filled pipe of 5-inch (12.7 cm) diameter the lowest cutoff frequency for the higher mode is ~7 kHz assuming the velocity in the liquid is 1500 m/s, which is typical of a fluid like water. The disclosed invention comprises modems with three different acoustic transducer configurations as will now be described.

Linear Phased Array Transducer

Figure 2:
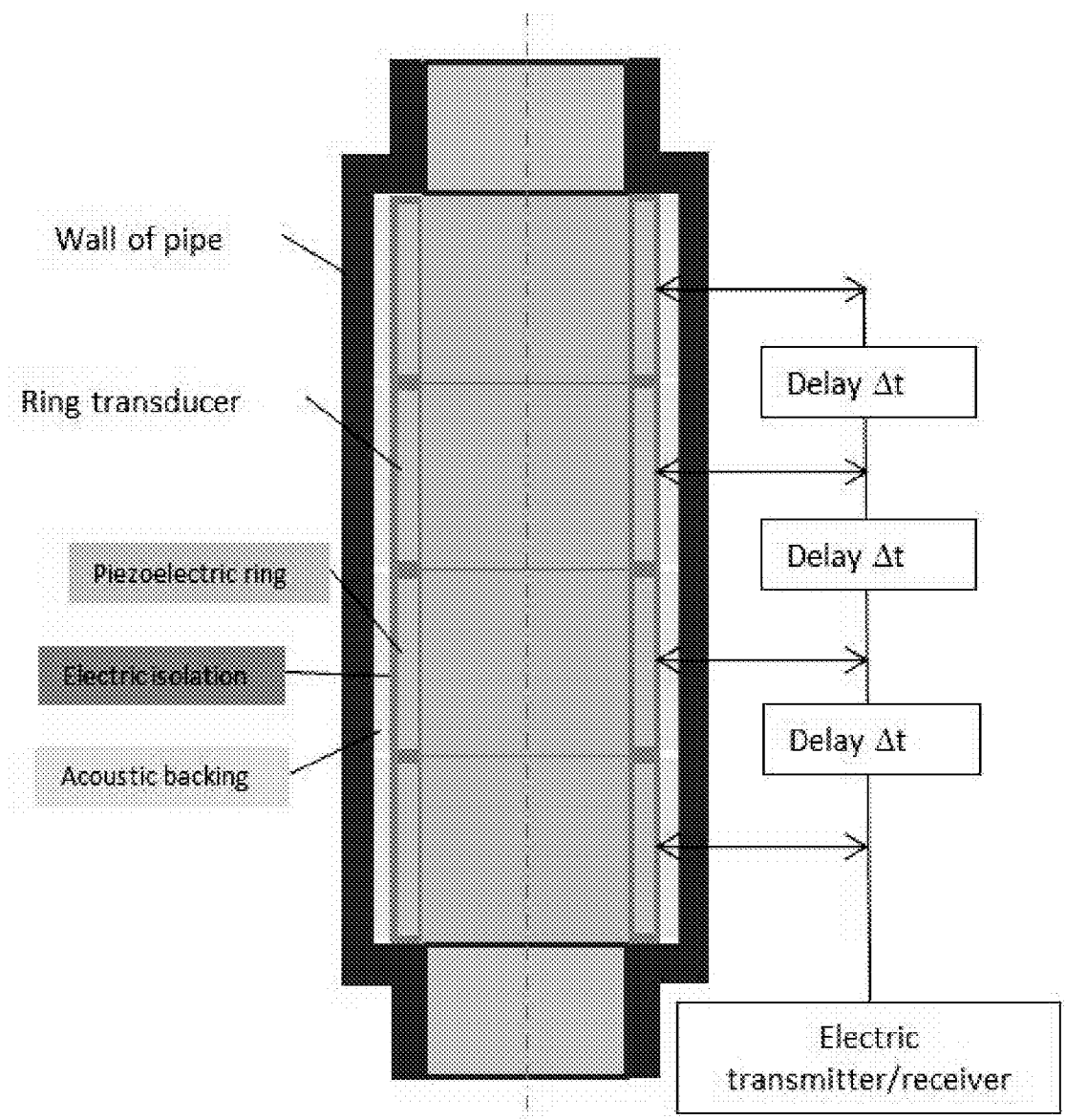
FIG. 2 is a schematic view of a phased array design for communication through the liquid filled pipe.

A linear phased array transducer is scanned electrically to produce an up or downhole signal as described below. FIG. 2 shows a schematic view of a phased array transmitter design for communication through the liquid filled pipe. The phased array transmitter comprises at least two ring transducers. An active piezoelectric ring is covered by an electric isolation layer and has an acoustic backing to minimize or to prevent radiating acoustic energy outside of the pipe. The frequency of the transducer may be adjusted to be lower than any high mode cutoff frequencies to avoid signal distortion that can be caused by different phase and group velocities of the high propagating modes in the liquid filled pipe and still maintain the benefit of relatively low propagating attenuation of the fundamental mode in the pipe. The inner surface of the transducer is conformed to the inner diameter of the pipe to avoid mechanical interference with the flow and the passing of down-hole instruments and to avoid the creation of extra local turbulence that is a noise source for a signal receiver. FIG. 2 shows the electronic transmitter or receiver that sends or receives signal in the upward direction. The delay time $t=V/L$, where V is the acoustical velocity of the liquid of the fundamental mode in the pipe, and L is the spacing between the centers of adjacent transducers. The height of the transducer should preferably be less than the half wavelength of the mode wave for high transmission efficiency. The transmitted acoustic signals from the transducers will be added when propagating upward in the pipe but can create phase cancellation in the downward direction in the working frequency range. A similar response can be achieved when an array functions as an acoustic receiver. The cancellation can be optimized by adjusting the number and spacing of the transducers. In some embodiments, the time delay stages can be replaced by phase shifters. As is well understood, a difference in time and a difference in phase are equivalent, and can be interrelated if one is given the characteristics of the signals being applied to a phased array system.

Figure 3:
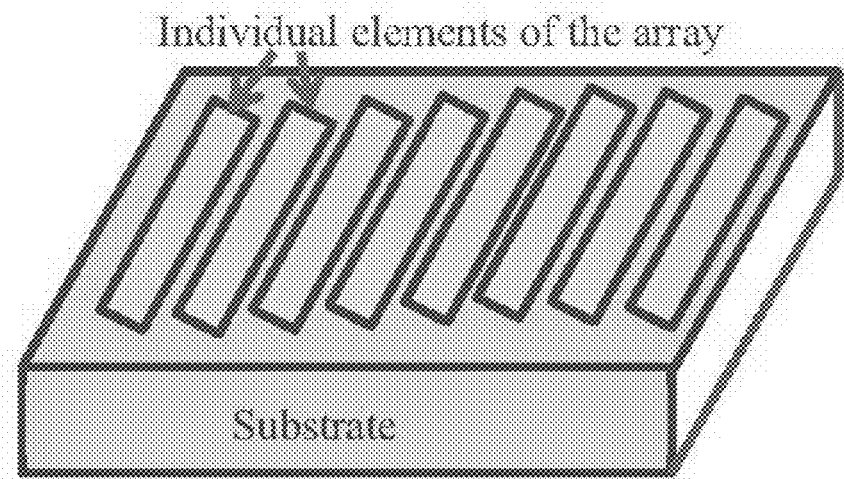
FIG. 3 is a schematic view of a phased array transducer and its elements.

Generally, conventional acoustic and ultrasonic transducers comprise either a single active element that both generates and receives the sound waves, or two paired elements in which one is used for transmission and the other element is used for reception. In contrast, phased array transducers are made as a planar assembly of multiple small individual elements, as illustrated in FIG. 3, each one of which can be pulsed individually. By controlling the phase of the transmitted wave of each of the individual elements, interference takes place to create a wave having controlled directivity. Specifically, by controlling the time delay between the trigger of the emitted signal applied to each successive element, the emitted sound waves can form a beam that can be directed over a range of desired angles.

Figure 4A:
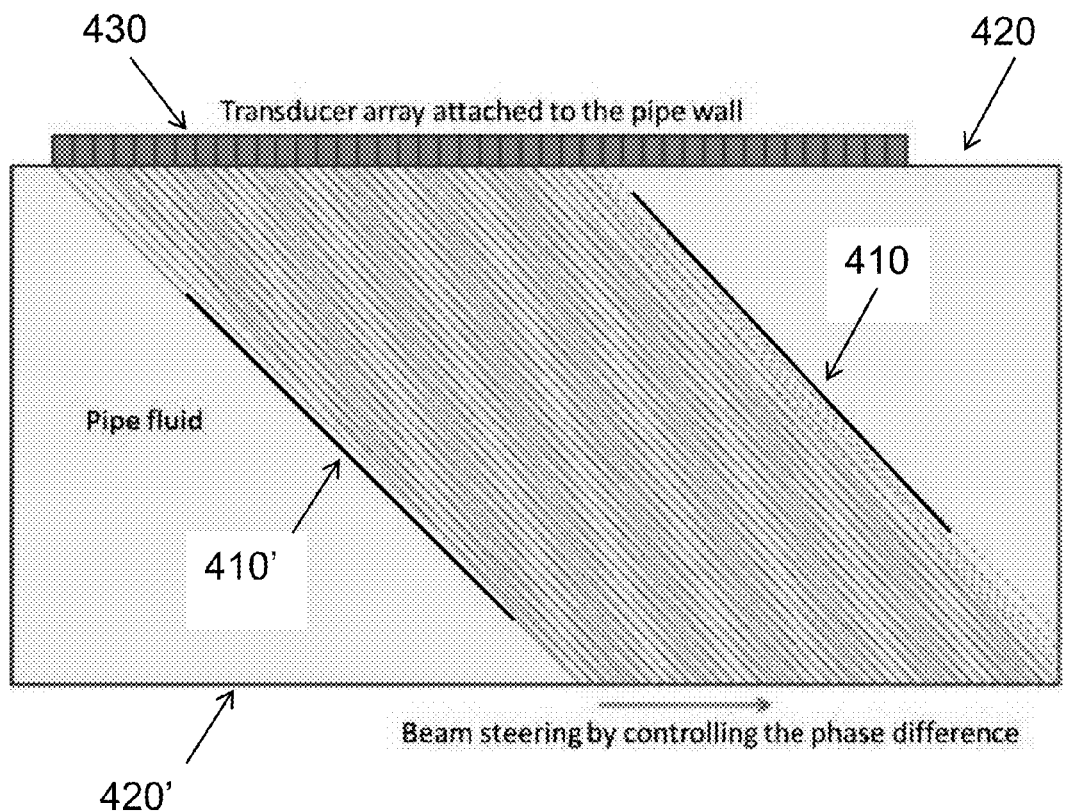
FIG. 4A is a schematic view of the activation of a phased array transducer that emits a beam at an angle by controlling the time delay of the transducer elements.

FIG. 4A is a schematic view of the activation of a phased array transducer in a sweeping mode by controlling the time delay from the transducer elements. In FIG. 4A the lines 410, 410' denote such a directed beam that propagates at an angle across the pipe, whose walls are dented 420, 420'. The transmitter phased array is denoted by 430. Thus, an acoustic wave transmission at an angle that can range from close to +90° to the surface of the array close to −90° to the surface of the array can be generated. The signals can be received by another phased array transducer at a distance from the transmitter along the surface of the pipe.

Figure 4B:
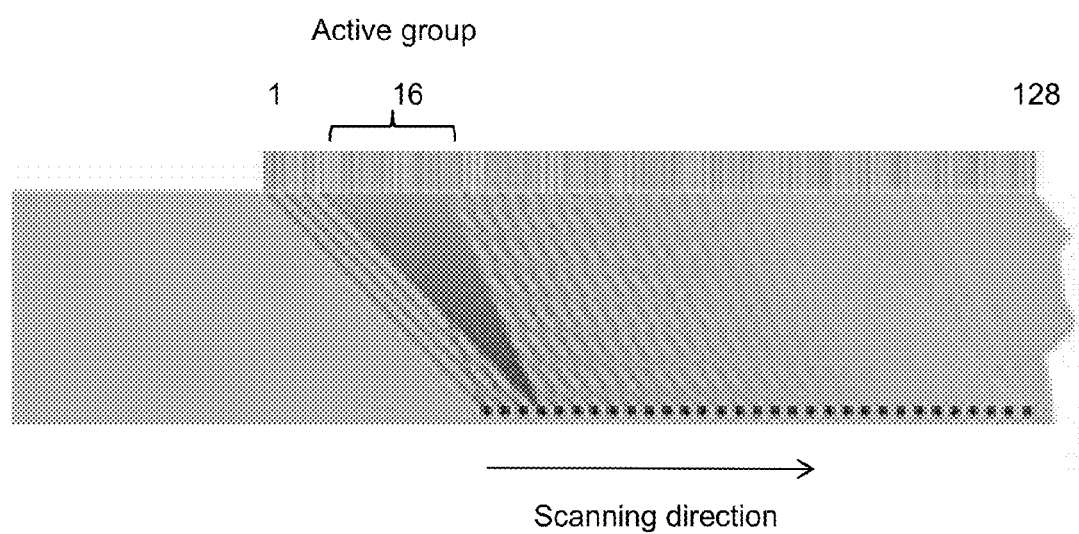
FIG. 4B is a schematic view of the activation of a phased array transducer in a sweeping mode by controlling the time delay of the transducer elements
Figures 5A, 5B:
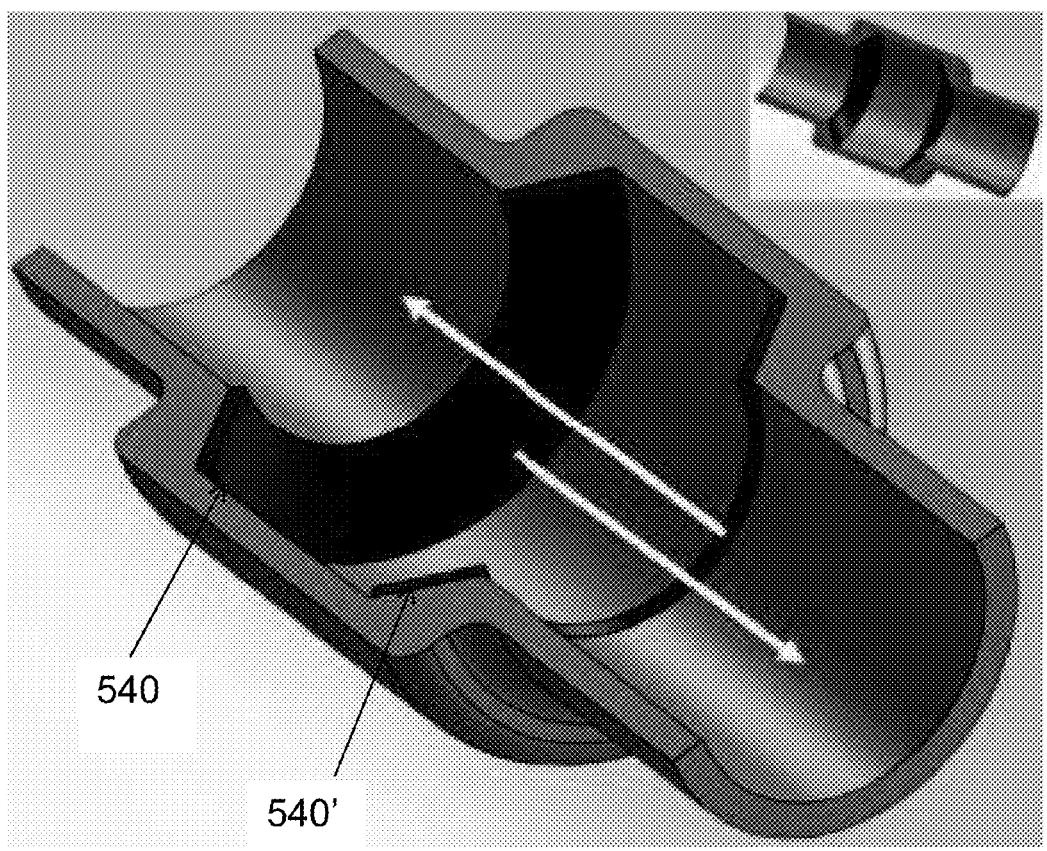
FIG. 5A is a schematic cross-sectional view of a dual angled piezoelectric ring transducer design. Arrows show direction of signal transmitted from each transducer. The transducers can sense signals from the opposing direction.
FIG. 5B is another view of the transducer in FIG. 5A.

FIG. 4B is a schematic view of the activation of a phased array transducer in a sweeping mode by controlling the time delay of the transducer elements Directional Transducers Another method of producing up-hole or down-hole ultrasonic/sonic communication signals is to use an angled piezoelectric ring (or segmented ring) transducer. FIG. 5A is a schematic cross-sectional view of a dual angled piezoelectric ring transducer design that has a normal surface predominately facing up-hole (540) or down-hole (540'). Arrows show direction of signal transmitted from each transducer. The transducers can sense signals from the opposing direction. The up pipe transducer or the down pipe transducer can be switched individually on or at the same time to send a signal up or down the hole. In one embodiment, the ring transducers can be designed with Solid Micro Horn Array SMIHA matching layers to increase the power transmitted and reduce the reflected signal. See Stewart Sherrit, Xiaoqi Bao, Yoseph Bar-Cohen, "Solid Microhorn Arrays for Acoustic Impedance Matching", Proceedings of the SPIE 15th International Symposium on Smart Structures and Materials, San Diego, Calif., SPIE Vol. 6932-107, 9-13 Mar., 2008 and Stewart Sherrit, Xiaoqi Bao, Yoseph Bar-Cohen, "Micro-Horn Arrays for Ultrasonic Impedance Matching" NPO-43907, NASA Tech Briefs, Vol. 33, No. 9, pp. 46-47, September 2009. It is believed that the transducer pair can be used to measure a signal sent from above the section and transmit information down a section or vice versa. The transducers shown will also generate ultrasonic waves in the pipe that travel at much faster speeds and these signal may be used to corroborate the signals that are transmitted through the oil.

Bi-Directional Volume Expanding Transducer

Figure 6:
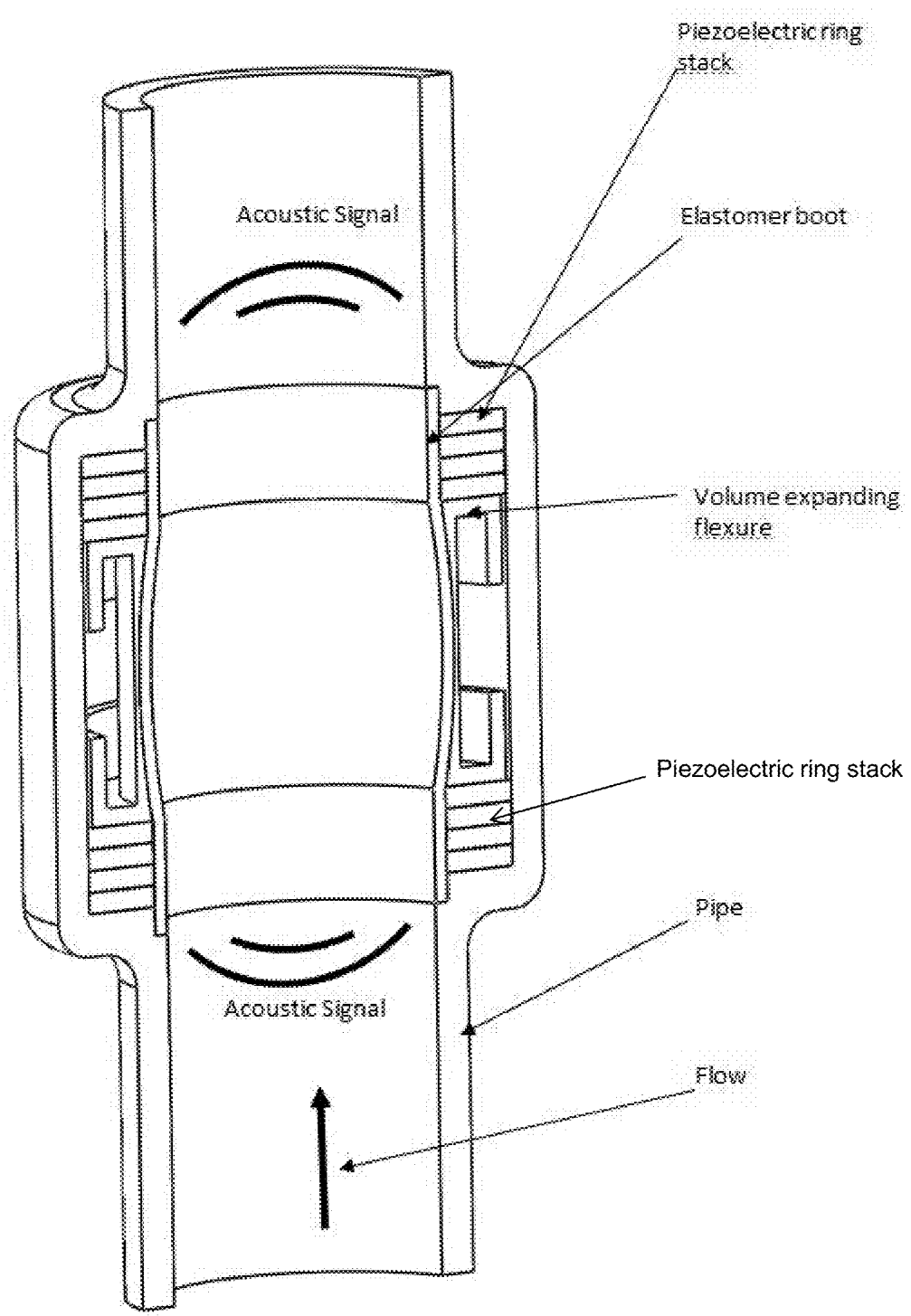
FIG. 6 is a schematic view of a bi directional volume expanding transducer that produces an alternative pressure that travels both up and down a pipe. It also can be an element of phased array that could be configured to transmit or receive acoustical signals in one direction.

FIG. 6 is a schematic view of a bi directional volume expanding transducer that produces an alternative pressure that travels both up and down a pipe. This transducer simultaneously transmits acoustic signals up and down the pipe. The transducer comprises piezoelectric rings in one or more stacks, and a metal flexure. When the transducer is excited, the one or more piezoelectric ring stacks expand and contract, and in turn compress the metallic flexure and allow it to return to an uncompressed state. When compressed, the flexure pushes the elastomeric boot into the pipe and creates a pressure wave that propagates up and down the pipe. The pressure wave is generated at the same frequency as that of the excited piezoelectric ring stack. These could be singular transducer elements or configure in a cylindrical linear array along the pipe length.

System Components and Communications Elements

As used herein, the phrase "phased array acoustic communication device" (or "PAACD") is intended to mean a communication device that comprises a phased array of acoustic transducers of at least one of the types described herein, along with a power supply, a general purpose programmable computer, and a set of instructions recorded on a machine-readable medium configured so that the device can receive and transmit acoustic signals, can encode, decode and process information coming from and/or going to another PAACD or a sensor, and can operate autonomously (e.g., does not have to be supported by another device) when required to operate autonomously.

Figures 7A, 7B, 7C:
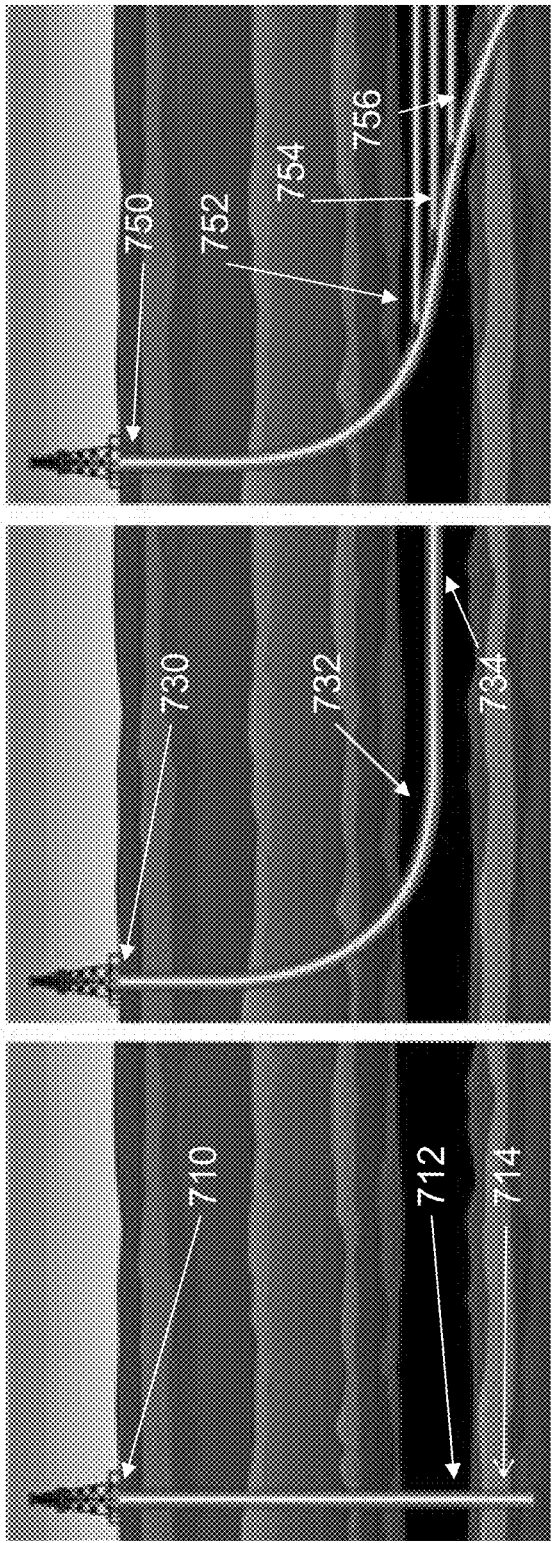
FIG. 7A is a schematic diagram of a vertical well.
FIG. 7B is a schematic diagram of a stand-alone horizontal well.
FIG. 7C is a schematic diagram of a multi-lateral well.

FIG. 7A is a schematic diagram of a vertical well. In FIG. 7A, there is a phased array acoustic communication device 710 at the top of the well, and one or more phased array acoustic communication devices 712, 714 at various depths in the well.

FIG. 7B is a schematic diagram of a stand-alone horizontal well. In FIG. 7B, there is a phased array acoustic communication device 730 at the top of the well, and one or more phased array acoustic communication devices 732, 734 at various positions along the bore of the well.

FIG. 7C is a schematic diagram of a multi-lateral well. In FIG. 7C, there is a phased array acoustic communication device 750 at the top of the well, and one or more phased array acoustic communication devices 752, 754, 756 at various positions along the bore of the well, which can be locations along different branches of the bore.

Figure 8:
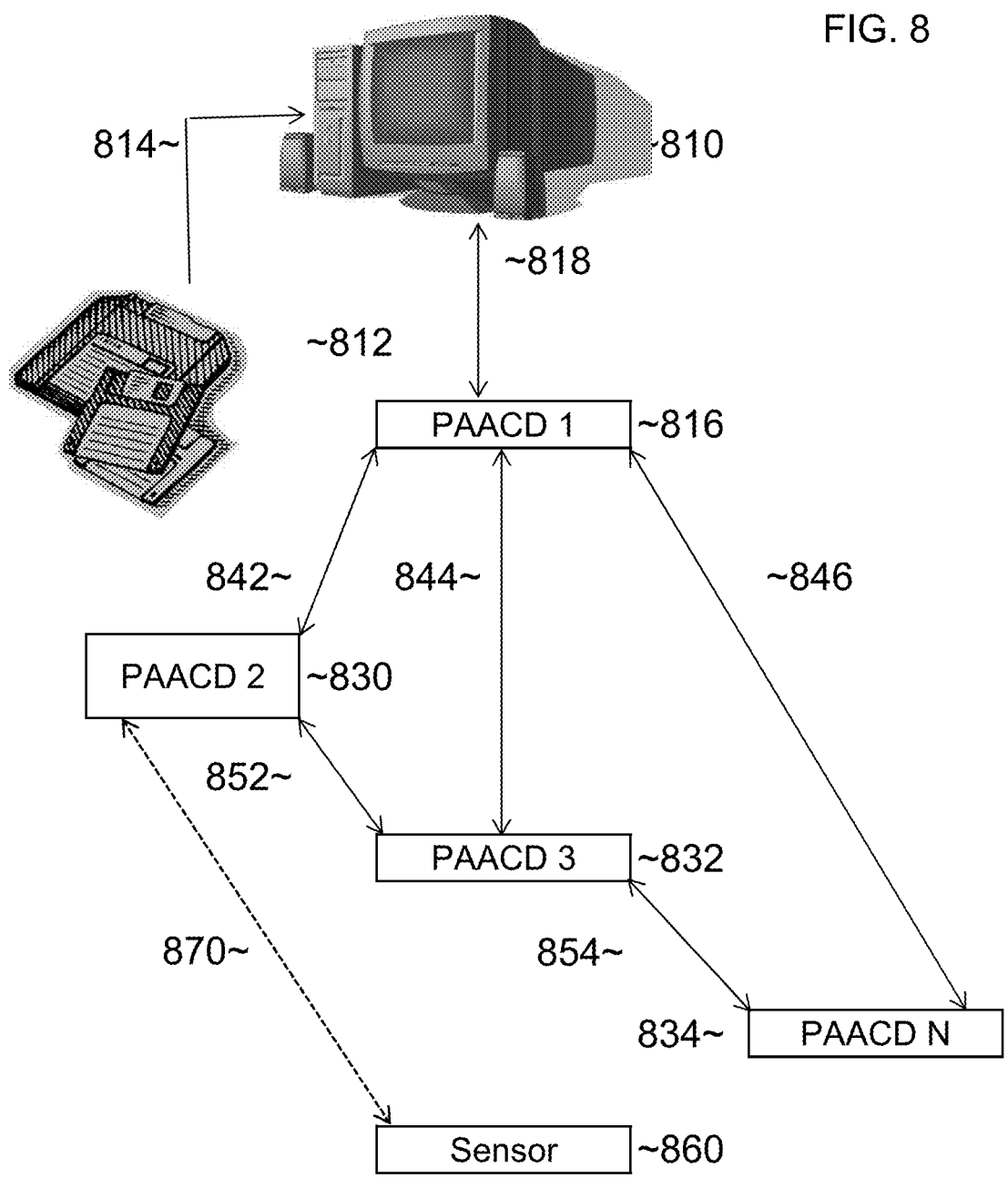
FIG. 8 is a schematic diagram of a controller in communication with a plurality of phased array acoustic communication devices and a sensor.

FIG. 8 is a schematic diagram of a controller in communication with a plurality of phased array acoustic communication devices and a sensor. As illustrated in FIG. 8, in one embodiment the controller is a computer-based controller 810, such as a general purpose programmable computer that can be programmed with instructions recorded in a non-volatile manner on a machine-readable medium 812 such as a magnetic disk. The instructions can be communicated from the machine-readable medium 812 to the computer-based controller 810, for example as illustrated by arrow 814, which can denote that the machine-readable medium 812 is physically connected to the computer-based controller 810, or is in electronic communication with the computer-based controller 810.

When operating on the computer-based controller 810, the instructions recorded in non-volatile fashion on the machine-readable medium 812 define methods of operating a plurality of phased array acoustic communication devices 816, 830, 832, 834. In general, at least two phased array acoustic communication devices 812, 830 are provided. Phased array acoustic communication device 816 (also referred to as phased array acoustic communication device 1 or the phased array acoustic communication device at the top of the well) is in bi-directional communication with controller 810 as designated by bi-directional arrow 818. Communication between the computer-based controller 810 and phased array acoustic communication device 816 can be performed using any convenient digital protocol, for example any of the IEEE 802 protocols, the International Telecommunications Union (ITU) H.323 protocol, or the Integrated Services Digital Network (ISDN) protocol. The bi-directional communication can be by way of a wired electrical connection, a wireless connection, a fiber optic connection, or any other conventional communication connection. The physical distance between controller 810 and phased array acoustic communication device 816 can be any convenient distance.

The computer-based controller 810 can receive instructions or commands from a user, who can issue such instructions or commands using a device such as a keyboard, a mouse, a touchscreen or any convenient human interface device that communicates with the computer-based controller 810.

The user can be situated proximate to the computer-based controller 810, or can be remote from the computer-based controller 810 and connected to the computer-based controller 810 using a packet-based communication system such as the Internet.

The computer-based controller 810 can include a display. If a user is proximate to the computer-based controller 810, the display can be used to show the user the progress of the communications that are taking place. If the user is remote from the computer-based controller 810, the information to be displayed can be communicated to a display proximate to the user's location. In particular, either display can be configured to display to the user information indicative of the communications that are taking place.

Phased array acoustic communication device 816 can communicate using the acoustic methods of the invention with one or more of phased array acoustic communication devices 830, 832, . . . 834 (indicated as phased array acoustic communication devices 2, 3, and N where N is an integer greater than or equal to 4) in a direct manner (indicated by bi-directional arrows 842, 844 and 846, respectively), or indirectly by using a communication link between two of the other phased array acoustic communication devices (indicated by bi-directional arrows 852, 854).

In order to effectuate communication, each phased array acoustic communication device includes a local processor, such as a microprocessor or a microcontroller, a local memory such as a semiconductor memory, and a local power supply, such as a battery. Each phased array acoustic communication device can be assigned a unique identification, such as a unique alphanumeric string. Alternatively, each transducer can use a unique operating frequency as an identifier. Communication can be carried out according to an agreed protocol, such as a packet-based digital protocol communicated by way of acoustic signals between the phased array acoustic communication devices.

One sensor 860 is illustrated in FIG. 8, which is shown as being in bidirectional communication with phased array acoustic communication device 830 by way of dotted arrow 870. The dotted arrow is used to indicate a communication link that is possibly switchable to another of the phased array acoustic communication devices, depending on which one is closest to sensor 860.

Figure 9:
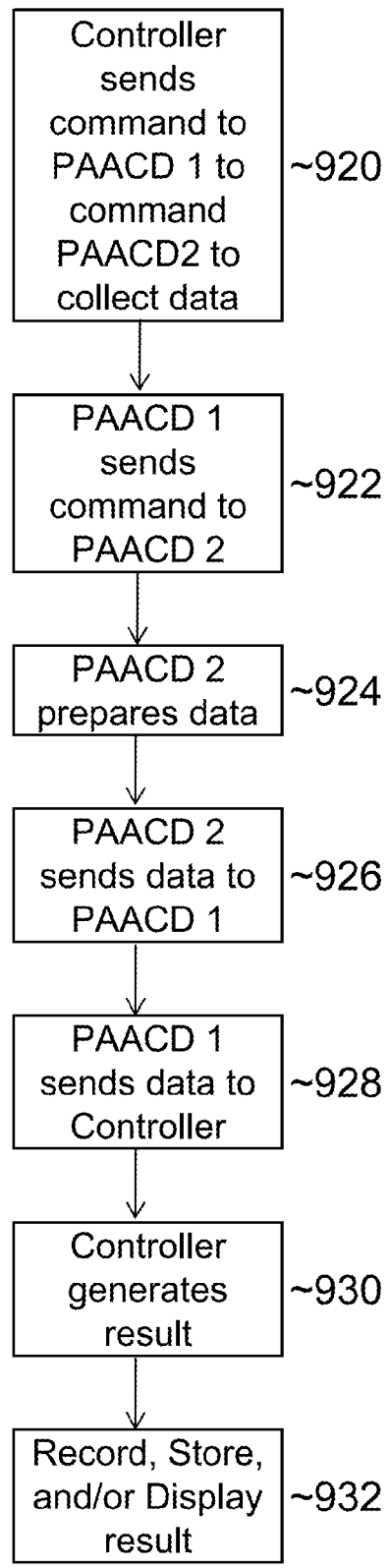
FIG. 9 is a schematic flow diagram of a data collection process.

FIG. 9 is a schematic flow diagram of a data collection process. As illustrated in FIG. 9, at step 920 a command is issued by a controller, such as the computer-based controller 810. The command can be in response to a directive from a user, or it can be issued based on an instruction in a set of instructions recorded on machine-readable medium 812. The command directs phased array acoustic communication device 1 to communicate an instruction to another phased array acoustic communication device to collect data and/or to report data already collected. At step 922 phased array acoustic communication device 1 sends an appropriate command to a second phased array acoustic communication device, such as phased array acoustic communication device 2 (or, as will be understood from FIG. 8, any other phased array acoustic communication device as needed), which command instructs the receiving phased array acoustic communication device to perform specified actions. At step 924 the second phased array acoustic communication device performs the necessary actions, for example, to prepare data. At step 926 the second phased array acoustic communication device sends the data to the first phased array acoustic communication device. At step 928 the first phased array acoustic communication device sends the data to the controller. At step 930 the controller generates a result from the data, which is digital data, such as analyzing the data or converting the data to a form needed by the user, such as textual, numerical or graphical data. At step 932 the result is recorded, and/or stored, and/or displayed.

Figure 10:
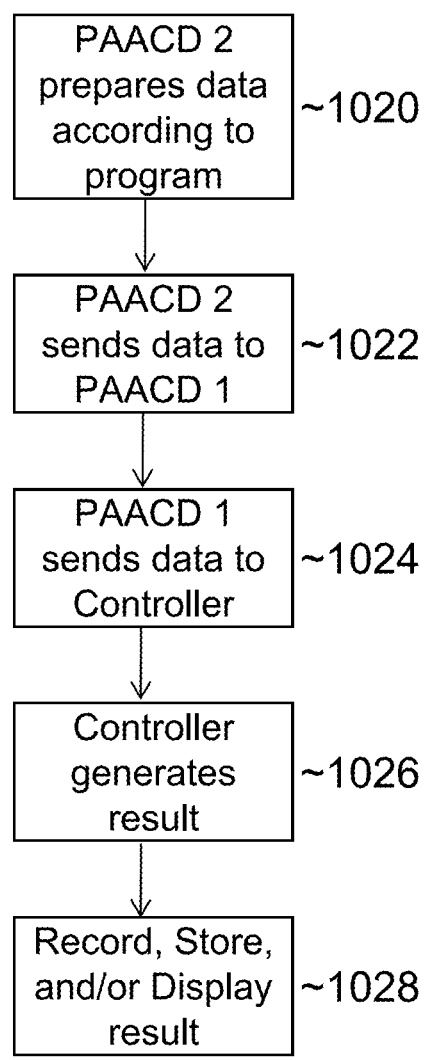
FIG. 10 is a schematic flow diagram of an alternative data collection process.

FIG. 10 is a schematic flow diagram of an alternative data collection process. In the process of FIG. 10, at step 1020 the second phased array acoustic communication device (e.g., a phased array acoustic communication device located in a bore or well casing) prepares data according to a program (e.g., according to instructions recorded on a local machine-readable memory resident at the phased array acoustic communication device). At step 1022 the second phased array acoustic communication device sends the data to the first phased array acoustic communication device. At step 1024 the first phased array acoustic communication device sends the data to the controller. At step 1026 the controller generates a result from the data, which is digital data, such as analyzing the data or converting the data to a form needed by the user, such as textual, numerical or graphical data. At step 1028 the result is recorded, and/or stored, and/or displayed.

The acoustic transducer is an important component of the system and improves the communication from sensors as well as controlling actuators in the completion zone.

Data Rates and Data Volumes

In a first embodiment, the modem disclosed modulates an analog carrier signal to encode digital information, and also demodulates the carrier signal to decode the transmitted information. Thus, a signal can be transmitted and decoded to reproduce the original digital data.

In a second embodiment, the modem can use pulsed signals comprising a plurality of cycles at an operating frequency to encode and to decode information. In such a system, pulses and spaces between the pulses are used to encode information according to a predefined protocol.

The data rate that can be expected is in the range of up to the tens of kilo-Hertz range. The information that can be communicated includes the standard information that is conventionally logged for wells, such as the status of the well, the geological conditions of the environment surrounding the borehole, flow rate of oil or gas, and any other information that sensors are available to provide.

Speed of Sound

As will be appreciated, acoustic communication relies on the propagation velocity of acoustic signals. The speed of sound in various media is presented in the following Table 1.

TABLE 1

| Material | Formula for calculating speed of sound | MKS units (M/s) |
|---|---|---|
| Air | $c_{air} = 331.3 \text{ m} \cdot \text{s}^{-1} \sqrt{1 + \frac{\vartheta}{273.15}}$ | 343.2 m/s |
| Fresh water | $c_{fluid} = \sqrt{\frac{K}{\rho}}$ | 1497 m/s |
| Salt water | | 1560 m/s |
| Solid | $c_l = \sqrt{\frac{K + \frac{4}{3}G}{\rho}} = \sqrt{\frac{Y(1-v)}{\rho(1+v)(1-2v)}}$ $c_s = \sqrt{\frac{G}{\rho}}$ | Varies in the range of a few kilometers per second. |

For fluids such as air and water, the parameters given in the formulas are as follows: θ (theta) is the temperature in degrees Celsius (° C.); ρ is the density of the fluid; and K is the bulk modulus of the fluid.

For a solid, which is modeled as an elastic material, the parameters given in the formula are as follows: K and G are the bulk modulus and shear modulus of the elastic materials, respectively, Y is the Young's modulus, and v is Poisson's ratio. In particular the relation between Young's modulus and Poisson's ratio is given by $$Y=3K(1-2v).$$

According to U.S. Pat. No. 6,672,163, the speed of sound for liquids is in the range of 0.8 mm/μsec (or 800 m/s) to 2 mm/μsec (or 2000 m/s).

Therefore, it is apparent that an acoustic signal from a source in a well will typically take from fractions of a second (for signal sources close to the surface) to a few seconds (for sources several kilometers deep in a well) to travel to a receiver located at the surface. The time to transmit a signal in the opposite direction will also require a similar time of travel to propagate from a source at the surface to a receiver located some distance downhole.

In some instances, it may be necessary to "relay" a signal by providing a plurality of phased array acoustic communication devices, located at different distances along the borehole, so that a signal from a source deep in the borehole can be received by a phased array acoustic communication device closer to the surface, amplified, and retransmitted to another phased array acoustic communication device closer to (or at) the surface, so as to provide sufficient signal amplitude to transmit information successfully and with an acceptably low error rate. The same method of "relaying" a signal can also be used in the downward direction (e.g., from the surface to a phased array acoustic communication device located at some distance down the borehole). The delay in the electronic data handling will be very short (e.g., of the order of microseconds or less per phased array acoustic communication device). The delay in conversion of a signal between an electrical signal and an acoustic signal as performed by a phased array acoustic communication device will be of the order of a few acoustic cycles at the frequency of operation, which is of the order of milliseconds at kilohertz frequencies. Therefore, the delays due to propagation are generally going to be the rate limiting delays in the system.

In some embodiments, it is expected that the delay will be of the order of a few seconds to a few tens of seconds for a "round-trip" propagation of a signal.

Power Supplies

Power systems used in measuring while drilling systems (MWD) generally may be classified as one of two types: battery or turbine. Both types of power systems have inherent advantages and liabilities. In many MWD systems, a combination of these two types of power systems is used to provide power to the MWD tool so power will not be interrupted during intermittent drilling-fluid flow conditions. Batteries can provide this power independent of drilling-fluid circulation, and they are necessary if logging will occur during tripping in or out of the hole.

Lithium-thionyl chloride batteries are commonly used in MWD systems because of their excellent combination of high-energy density and superior performance at MWD service temperatures. They provide a stable voltage source until very near the end of their service life, and they do not require complex electronics to condition the supply. These batteries, however, have limited instantaneous energy output, and they may be unsuitable for applications that require a high current drain. Although these batteries are safe at lower temperatures, if heated above 180° C., they can undergo a violent, accelerated reaction and explode with a significant force. Even though these batteries are very efficient over their service life, they are not rechargeable, and their disposal is subject to strict environmental regulations. Alternatively, one can use secondary (or rechargeable) batteries.

The second source of abundant power generation, turbine power, uses the rig's drilling-fluid flow as an energy source (or to transmit energy from a power source at the well head to a device that consumes power downhole). A turbine uses the mud flow to generate rotational motion. Rotational force is transmitted by a turbine rotor to an alternator through a common shaft, generating a three-phase alternating current (AC) of variable frequency. Electronic circuitry rectifies the AC into usable direct current (DC). The excess current can be used to recharge a rechargeable battery.

Computer Control of Operation

Commercially available data acquisition and analysis packages such as LabView®, LabWindows™/CVI software and PXI hardware (available from National Instruments Corporation, 11500 N. Mopac Expwy, Austin, Tex. 78759-3504) can be used to receive, log and analyze data, and control the operation of hardware, using a general purpose programmable computer. This has been reported in the literature for some years. One of ordinary skill can construct and operate such systems with minimal need for experimentation.

DEFINITIONS

Unless otherwise explicitly recited herein, any reference to an acoustic signal, an electronic signal or an electromagnetic signal (or their equivalents) is to be understood as referring to a non-transitory acoustic signal, a non-transitory electronic signal or a non-transitory electromagnetic signal.

Recording the results from an operation or data acquisition, such as for example, recording results at a particular frequency or wavelength is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use, so that the result can be displayed, recorded to a non-volatile memory, or used in further data processing or analysis.

THEORETICAL DISCUSSION

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. An acoustic communication system for use in a tubulation, comprising:
   a tubulation having a first end and at least a second end;
   a plurality of bidirectional phased array acoustic communication devices, each of said plurality of bidirectional phased array acoustic communication devices configured to send acoustic signals and to receive acoustic signals, a first one of said plurality of bidirectional phased array acoustic communication devices situated proximate to said first end of said tubulation and having at least one input port for communication with a controller and having at least one output port for communication with said controller, and a second one of said plurality of bidirectional phased array acoustic communication devices situated at a distance along said tubulation from said first one of said plurality of bidirectional phased array acoustic communication devices, said second one of said plurality of bidirectional phased array acoustic communication devices configured to communicate with and to receive instructions by way of said first one of said plurality of bidirectional phased array acoustic communication devices; and
   said controller configured to activate said first one of said plurality of bidirectional phased array acoustic communication devices by way of said at least one input port, configured to receive a signal from said first one of said plurality of bidirectional phased array acoustic communication devices by way of said at least one output port and configured to provide at a controller output port an electrical signal representative of an acoustic signal received by said first one of said plurality of bidirectional phased array acoustic communication devices;
   said plurality of bidirectional phased array acoustic communication devices and said controller configured to communicate using a digital communication protocol,
   wherein the tubulation comprises a plurality of angled wall sections extending at an angle relative to a local longitudinal axis of the tubulation, and each bidirectional phased array acoustic communication device of the plurality of bidirectional phased array acoustic communication devices is located at a corresponding angled wall section of the plurality of angled wall sections.

2. The acoustic communication system for use in a tubulation of claim 1, wherein said tubulation is a bore of a well.

3. The acoustic communication system for use in a tabulation of claim 2, wherein a transducer system does not occlude or obstruct said bore of said well.

4. The acoustic communication system for use in a tubulation of claim 1, wherein each of said plurality of bidirectional phased array acoustic communication devices has a unique identifier used in communication between phased array acoustic communication devices.

5. The acoustic communication system for use in a tubulation of claim 1, wherein each of said plurality of bidirectional phased array acoustic communication devices operates at an acoustic frequency different from the acoustic frequency of operation of all others of said plurality of bidirectional phased array acoustic communication devices.

6. The acoustic communication system for use in a tubulation of claim 2, wherein the well is an oil well.

7. The acoustic communication system for use in a tubulation of claim 2, wherein the well is a gas well.

8. The acoustic communication system for use in a tubulation of claim 1, wherein the controller comprises a general purpose programmable computer and a set of instructions recorded in a non-transitory manner on a machine-readable medium.

9. The acoustic communication system for use in a tubulation of claim 8, wherein the set of instructions when operating on the general purpose programmable computer activates said first one of said plurality of bidirectional phased array acoustic communication devices by way of said at least one input port.

10. The acoustic communication system for use in a tubulation of claim 8, wherein the set of instructions when operating on the general purpose programmable computer controls the reception of a signal from said first one of said plurality of bidirectional phased array acoustic communication devices by way of said at least one output port.

11. The acoustic communication system for use in a tubulation of claim 8, wherein the set of instructions when operating on the general purpose programmable computer controls the provision at a controller output port of an electrical signal representative of an acoustic signal received by said first one of said plurality of bidirectional phased array acoustic communication devices.

12. The acoustic communication system for use in a tubulation of claim 8, further comprising a display.

13. The acoustic communication system for use in a tubulation of claim 12, wherein the set of instructions when operating on the general purpose programmable computer controls the operation of the display.

14. The acoustic communication system for use in a tubulation of claim 12, wherein the set of instructions when operating on the general purpose programmable computer controls the information that will be presented to a user.

15. The acoustic communication system for use in a tubulation of claim 8, further comprising an input device operable by a user.

16. The acoustic communication system for use in a tubulation of claim 15, wherein the set of instructions when operating on the general purpose programmable computer controls the receipt of input from a user.

17. The acoustic communication system for use in a tubulation of claim 1, wherein at least one of said plurality of bidirectional phased array acoustic communication devices is in tubular form.

18. The acoustic communication system for use in a tubulation of claim 1, wherein at least one of said plurality of bidirectional phased array acoustic communication devices has an internal opening of at least said same cross section as said tubulation.

19. The acoustic communication system for use in a tubulation of claim 1, wherein at least one of said plurality of bidirectional phased array acoustic communication devices is in communication with a sensor.

20. The acoustic communication system for use in a tubulation of claim 1, wherein said digital communication protocol is a protocol selected from the group consisting of an Institute of Electrical and Electronics Engineers (IEEE) 802 protocol, an International Telecommunications Union (ITU) H.323 protocol, an Integrated Services Digital Network (ISDN) protocol and a packet-based digital protocol.

21. The acoustic communication system for use in a tubulation of claim 1, wherein the plurality of bidirectional phased array acoustic communication devices comprises piezoelectric transducers.

22. The acoustic communication system for use in a tubulation of claim 1, wherein the tubulation comprises at least one section having a metal flexure, an elastomeric boot and a plurality of piezoelectric rings configured to act on the metal flexure, the metal flexure in turn acting on the elastomeric boot to create pressure waves in a fluid within the tubulation.

* * * * *